United States Patent [19]
Welniak et al.

[11] Patent Number: 5,443,982
[45] Date of Patent: Aug. 22, 1995

[54] METHODS FOR THE CULTIVATION OF INFECTIOUS LARYNGOTRACHEITIS VIRUS

[75] Inventors: Ellan Welniak, Eagan; Gary R. Petersen, Lakeville, both of Minn.

[73] Assignee: Solvay Animal Health, Inc., Mendota Heights, Minn.

[21] Appl. No.: 91,826

[22] Filed: Jul. 13, 1993

[51] Int. Cl.$^6$ ...................... C12N 7/02; A61K 39/245
[52] U.S. Cl. .................. 435/235.1; 435/239; 435/240.2; 424/229.1; 424/816
[58] Field of Search .............. 424/89, 229.1, 816; 435/240.2, 235.1, 239

[56] References Cited

U.S. PATENT DOCUMENTS

| | | | |
|---|---|---|---|
| 3,331,736 | 7/1967 | Gelenczei | 424/229.1 |
| 3,444,293 | 5/1969 | Hudson | 424/229.1 |
| 4,980,162 | 12/1990 | Honda et al. | 424/202.1 |

OTHER PUBLICATIONS

Condreay et al, "Efficient Duck Hepatitis B Virus Production by an Avian Liver Tumor Cell Line", Journal of Virology, vol. 64, Jul. 1990, pp. 3249–3258.

Kawaguchi et al, "Establishment and Characterization of a Chicken Hepatocellular Carcinoma Cell Line, LMH[1]", Cancer Research, vol. 47, Aug. 15, 1987, pp. 4460–4464.

Schnitzlein et al, Avian Diseases 38, 211, 1994.

Primary Examiner—Christine M. Nucker
Assistant Examiner—Julie Krsek-Staples
Attorney, Agent, or Firm—Oblon, Spivak, McClelland, Maier & Neustadt

[57] ABSTRACT

This invention involves a chemically transformed chicken hepatocyte derived cell line which is capable of efficiently supporting replication of infectious laryngotracheitis virus (ILTV) and methods for cultivating ILTV using this hepatocellular carcinoma cell line. The virus harvested from these continuous cell culture methods can be used as a vaccine against ILTV infection.

5 Claims, 3 Drawing Sheets

METHODS FOR THE CULTIVATION OF INFECTIOUS LARYNGOTRACHEITIS VIRUS

BACKGROUND OF THE INVENTION

Figure 1:
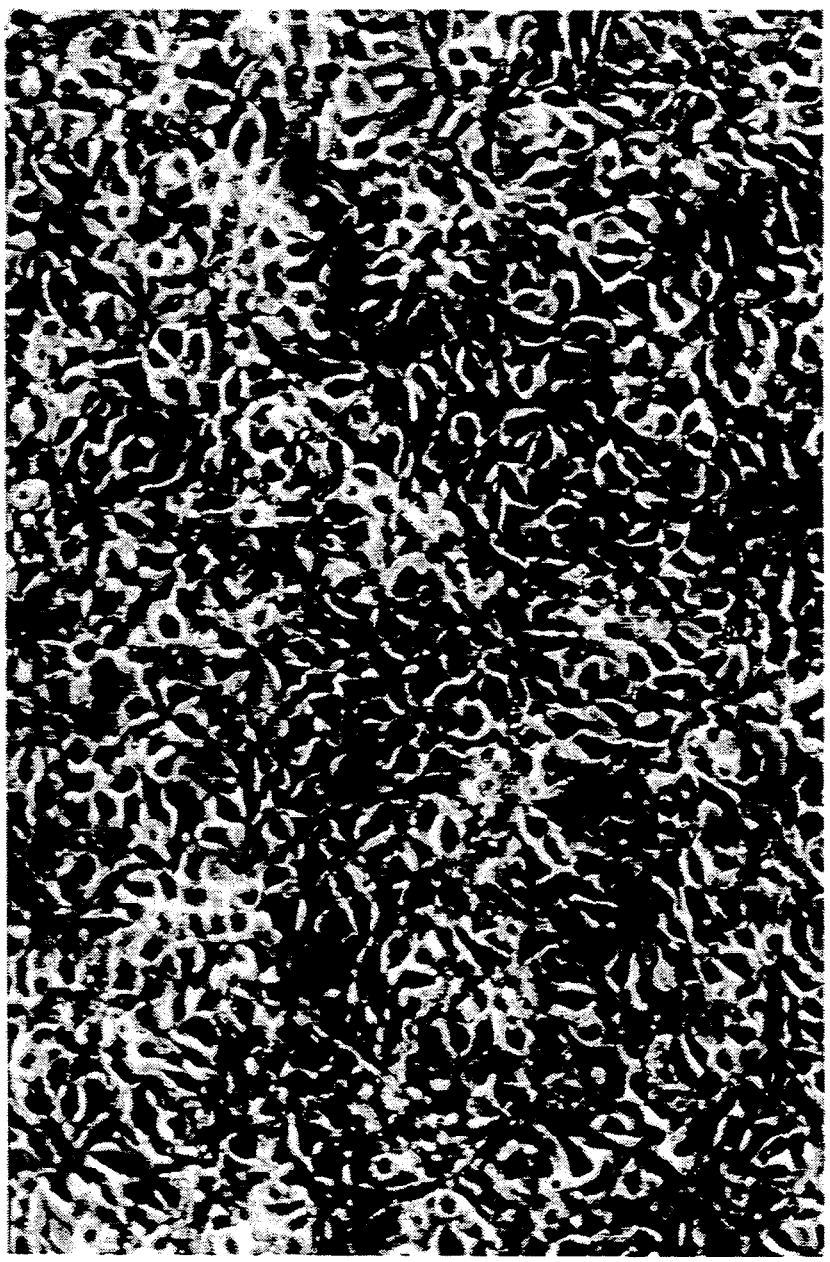
Figure 2:
Figure 3:
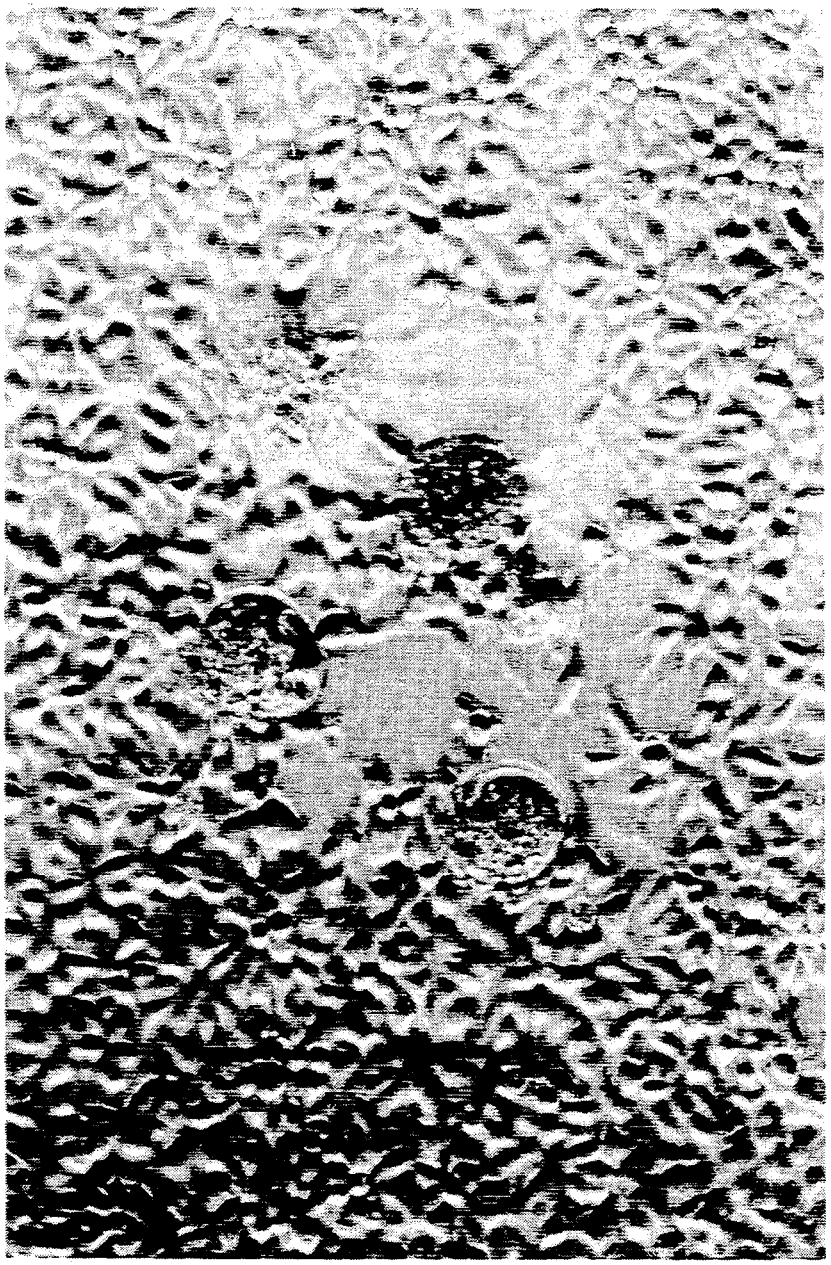

1. Field of the Invention:

This invention relates to methods for cultivating infectious laryngotracheitis virus and egg drop syndrome virus in a continuous cell line.

BACKGROUND OF THE INVENTION

Infectious laryngotracheitis virus (ILTV), the causative agent of a highly infectious upper respiratory tract disease in chickens, is a member of the family Herpesviridae, subfamily Alphaherpesviridae and was first identified in 1930. ILTV is highly contagious with mortality rates as high as 70% and is therefore of considerable economic importance. Immunization is the only efficient way to prevent this disease. Available vaccines against ILTV have relied on the cultivation of live artificially attenuated ILTV, naturally occurring nonpathogenic forms of the virus, or subunits of the virus. See for example, U.S. Pat. Nos. 3,444,293; 3,331,736; and 4,980,162 as well as patent applications WO 91 02053 and WO 92 03554 which all describe various ILTV vaccines.

Egg Drop Syndrome virus (EDS), the causative agent in a disease which is characterized mainly by a serious decrease in the egg production in laying hen flocks, is an adenovirus. During the past few years, this disease has become economically important in Western Europe where the virus was first isolated (Van Eck et al. (1976) Avian Pathology 5:261–272). Inactivated vaccines, which may impart immunity to the virus, have been produced in primary cells of duck embryo fibroblast (for example, U.S. Pat. No. 4,302,444).

ILTV has traditionally been cultivated in embryonic eggs and primary chicken cell cultures (Guo, P. (1982) Chinese J. Vet. Med. 8(7):18–20; Guo, P. (1982) J. South China Agri. Univ. 3(4):13–20), such as embryonic kidney (Chang et al. (1960) Avian Dis. 4:484–490), kidney (Mayer et al. (1967) Am. J. Vet. Res. 28(124):825–832) and embryonic liver (Hughes et al. (1988) Avian Pathol. 17:295–303) cells. Recent publications on ILTV show that it is still cultured in primary chicken cells (Griffin, A. (1991) J. Gen. Virol. 72:393–398; Kongsuwan et al. (1991) Virology 184:404–410; Keeler et al. (1991) Avian Dis. 35:920–929; Sheppard and York, (1991) Acta Virol. 34:443–448).

Likewise, recent publications on EDS show that it also is cultured in primary chicken cells (Zsak et al. (1981) J. Gen. Virol. 56:87–95; Todd et al. (1978) J. Gen. Virol. 40:63–75; Todd et al. (1988) Avian Pathology 17:909–919).

Preparation and maintenance of primary cell cultures are laborious and, therefore, time consuming enterprises requiring the sacrifice of many animals. Until now no continuous cell line has been identified which is capable of supporting either ILTV or EDS replication.

The advantages of a continuous cell line for the cultivation of ILTV and EDS in comparison to primary cells are many. Due to high multiplication rates, large numbers of cells are available within a short period of time. Demands on the complexity of culture medium are low. Continuous cell lines are easily maintained and passaged, and can be frozen for storage. Continuous cell line cultivation allows constant and more stringent parameter controls in experiments, while each preparation of primary cells imposes new parameters.

Continuous cell lines from different species have been established. However, considerable difficulty has been encountered when trying to obtain continuous culture cell lines from chicken tissues (Schneider et al. (1965) Exp. Cell Res. 39:631–636; Ponten, J. (1970) Int. J. Cancer 6:323–332; Gey et al. (1974) Exp. Cell Res. 84:63–71; Beug et al. (1977) Exp. Cell Res. 107:417–428; Kaji et al. (1979) Exp. Cell res. 119:231–236). More recently a number of continuous cell lines from chicken tissues have been described. These include lymphoblastoid cell lines from avian virus induced lymphomas (Akiyama and Kato, (1974) Biken J. 17:105–116; Hihara et al. (1974) Natl. Inst. Anim. Health Q. 14:163–173), or leukemias (Langlors et al. (1976) Cancer Res. 36:3894–3904; Pfeifer et al. (1980) Int. J. Cancer 25:235–242), fibroblastic cells from normal, Rous Sarcoma virus-treated or carcinogen-treated chicken embryo cells (Kaaden et al. (1982) In Vitro 18:827–834; Ogura et al. (1984) Gann. 75:410–414; Dinowitz, M. (1977) J. Natl. Cancer Inst. 58:307–312; Lerman et al. (1976) J. Natl. Cancer Inst. 57:295–301), and hepatocellular cells from carcinoma treated chickens (Kawaguchi et al. (1987) Cancer Res. 47:4460–4464). None of these cells have been suggested to be capable of supporting replication of either ILTV or EDS.

SUMMARY OF THE INVENTION

Accordingly, objects of the present invention include providing: methods for cultivating ILTV in a continuous cell line, a continuous cell line infected with ILTV, a vaccine for providing immunity against ILTV, methods for cultivating EDS in a continuous cell line infected with EDS, a continuous cell line, and a vaccine for providing immunity against EDS.

The present invention provides a method for obtaining infectious laryngotracheitis virus comprising (i) infecting a continuous avian hepatocellular cell line, wherein said cell line is CH-SAH, with infectious laryngotracheitis virus, (ii) culturing said virus, and (iii) recovering virus produced thereby.

The present invention also provides a method for obtaining egg drop syndrome virus comprising (i) infecting a continuous avian hepatocellular cell line, wherein said cell line is CH-SAH, with egg drop syndrome virus, (ii) culturing said virus, and (iii) recovering virus produced thereby.

BRIEF DESCRIPTION OF THE FIGURES

FIG. 1 Uninfected confluent monolayer of CH-SAH cells.

FIG. 2 Formation of multi-nucleated areas or syncytia following infection with ILTV.

FIG. 3 Progression of ILTV induced syncytia to stage of rounding up and detachment.

DETAILED DESCRIPTION OF THE PREFERRED EMBODIMENTS

Accordingly, the present invention provides a method for cultivating either ILTV or EDS in a hepatocellular carcinoma cell line (CH-SAH, which is alternatively called the LMH cell line). The CH-SAH cell line has been deposited with the American Type Culture Collection (ATCC), 12301 Parklawn Drive, Rockville, Md. 29852 under the provisions of the Budapest Treaty as accession number ATCC CRL 11354 on May 26, 1993. Growth of CH-SAH cells after passaging can be done in Waymouth, DMEM with glucose or fructose, DMEM/F-12 medium supplemented with L-glutamine, sodium bicarbonate, appropriate antibiotics (preferably gentamicin), calf serum and fetal calf serum. Suitable serum concentrations are 0%–20%. Cells can suitably be grown at a temperature range of from 35° to 40° C. (preferably 37°–38° C.) in a $CO_2$ incubator (preferably in an atmosphere containing 2%–5% $CO_2$). Alternatively, these cells can be grown in roller bottles, which provide a closed system without $CO_2$ exchange. CH-SAH cells flourish well at somewhat high density (see FIG. 1). CH-SAH cells can suitably be seeded at densities ranging from $5 \times 10^4$ to $5 \times 10^5$ cells/cm$^2$, preferably at $1 \times 10^5$ cells/cm$^2$ to $4 \times 10^5$ cm, and then split on day 3-7 with media. The media is preferably changed every 3-4 days. A suitable pH range is from 6 to 8 (preferably, 7.0 to 7.2). If the cells are grown in roller bottles, the seeding density is as described above and the cells are split on day 3-7 with 0-2 media changes during that period.

CH-SAH cells can suitably be infected with ILTV by known methods 3 to 24 hours after seeding. The same media and growth conditions as mentioned above for the propagation of these cells can be used to cultivate the infected cells. Suitable ILTV inoculum can be material grown in embryonated eggs, preferably chicken embryonated eggs, such as chorioallantoic membranes or allantoic fluid. Inoculum can alternatively be virus grown on CH-SAH cells. Preferably, inoculum is prepared by one or two cycles freezing at −70° C. followed by quick thawing to release viruses from infected cells. Inoculum can additionally be briefly sonicated. Absorption of the inoculum material onto the CH-SAH cells can be as brief as 1 hour. Alternatively, the inoculum can be left on the CH-SAH cells.

Following infection with ILTV, viral growth typically occurs after 24 to 48 hours. Morphological changes (cytopathic effect) in cell monolayers can be observed as a result of viral growth resulting in multinucleated areas, best described as syncytia (see FIG. 2). As these areas enlarge, the syncytia round up and detach from the vessel surface and begin to float in the supernatant (see FIG. 3).

Virus can suitably be harvested when the maximal cytopathic effect is observed. Suitable harvest methods include: agitation, aspiration, scraping, or freeze thawing accompanied by aspiration. Preferably, harvested viruses are stored at −70° C.

Harvested ILTV can suitably be titered either on CH-SAH cells, in embryonated eggs, or in primary cell cultures of embryonic kidney, kidney, or embryonic liver cells. 9–12 day old embryonated eggs are preferably used for virus titration. The inoculum is placed on the dropped chorioallantoic membrane (CAM). The inoculum is preferably made cell free and diluted in cell culture media or Tryptose phosphate broth.

Observation of ILTV cytopathic effect in cell cultures can be endpoint determined up to 7 days; this can suitably be done by visual evaluation of morphological changes on the monolayer or by fluorescent antibody staining techniques. Alternatively, observation of cytopathic effect in embryonated eggs can be visually evaluated by the detection of plaques on the CAM that have opaque edges and depressed central areas of necrosis. The plaques result from proliferation and necrosis of the affected cells in the CAM.

The activity of ILTV is suitably measured quantitatively by preparing dilutions of the sample and determining the highest dilution (endpoint) at which activity is still detectable. The preferred method is the Reed Muench method which permits interpretation of the 50% endpoint from data derived from a quantal response. The formula can be applied similarly to rates of infection in any host system. The unit of infectivity used to express the results are mean embryo infective dose, $EID_{50}$, and mean tissue culture infective dosed $TCID_{50}$.

CH-SAH cells can suitably be infected with EDS by known methods 24–72 hours, preferably 48 hours, after seeding. Growth of infected CH-SAH cells can be done in Waymouth, DMEM with glucose or fructose, DMEM/F-12 medium supplemented with L-glutamine, sodium bicarbonate, appropriate antibiotics (preferably gentamicin), calf serum and fetal calf serum. Suitable serum concentrations are 0%–20%. Cells can suitably be grown at a temperature range of from 35° to 40° C. (preferably 37°–38° C.) in a $CO_2$ incubator (preferably in an atmosphere containing 2%–5% $CO_2$). EDS infected CH-SAH cells can suitably be seeded at densities ranging from $5\times10^4$ to $5\times10^5$ cells/cm$^2$, preferably at $1\times10^5$ cells/cm$^2$ to $4\times10^5$ cm, and then split on day 3–7 with media. The media is preferably changed every 3–4 days. A suitable pH range is from 6 to 8 (preferably, 7.0 to 7.2).

Suitable EDS inoculum can be material grown in embryonic eggs, preferably duck embryonated eggs in the allantoic sac. Embryonic eggs are suitably inoculated by placing the inoculum on the allantoic sac. Alternatively, EDS inoculum can be virus grown in chicken embryo liver cells. Inoculum can alternatively be virus grown on CH-SAH cells. The inoculum is diluted, preferably in tissue culture medium, and brought in contact with the CH-SAH cells for 1 or more hours. Alternatively the inoculum can be left on the cells.

After infection of CH-SAH cells with EDS virus morphological changes in the cell culture occur. A cytopathological effect can be observed. Cells degenerate, become rounded and detach from the surface.

Virus can be harvested when the cytopathic effect is 50%. Methods include scraping, agitation or freeze thawing. Harvested virus fluids are preferably stored below −50° C.

Harvested EDS virus fluids can suitably be titrated in embryonated duck eggs, cell cultures of embryonic liver or kidney cells. Embryonated duck eggs, princubated 9–12 days, are preferably used for EDS virus titrations. The virus fluid is inoculated into the allantoic sac. Growth of EDS virus is monitored using the haemagglutination reaction. Titers are calculated using the Reed Muench method or the Spearmann-Karber method.

Having generally described this invention, a further understanding can be obtained by reference to certain specific examples which are provided herein for purposes of illustration only and are not intended to be limiting unless otherwise specified.

EXAMPLES

Example 1

The purpose of this experiment was to determine optimal parameters for propagation of CH-SAH cells in roller bottles. Parameters evaluated were roller bottle types, media volume and seeding densities.

CH-SAH cells were grown in DMEM/F-12 media supplemented with L-glutamine 0.2 mM, gentamicin 50 mg/ml and 10% non-heat inactivated, sterile filtered, fetal calf serum. A pool of cells were made from stock roller bottles that had been disassociated with 10% trypsin-EDTA and 90% saline A (saline with 10 gm/L glucose and 0.5% Phenol red). The cells were seeded on day 0 into roller bottles at a target density of $3\times10^5$ cells/cm$^2$. The manufacturers of the roller bottles were Corning (850 and 1700 cm$^2$), Falcon (850 and 1500 cm$^2$) and InVitro (1020 and 1700 cm$^2$). Media volumes per roller bottle were 350 ml/850 cm$^2$, 400 ml/1020 cm$^2$, 450 ml/1500 cm$^2$ and 450 ml/1700 cm$^2$. The roller bottles were incubated for 4 days at 37° C. with daily observation.

At the end of this time period, cells were harvested by trypsinization from each roller bottle. The individual roller bottle cell pool was then counted by tryphan blue staining.

| | Cell Yield/cm$^2$ | Yield |
|---|---|---|
| Corning 850 cm$^2$ | $1.383\times10^6$ | 4.6 X |
| Corning 1700 cm$^2$ | $7.964\times10^5$ | 2.7 X |
| Falcon 850 cm$^2$ | $1.265\times10^6$ | 4.0 X |
| Falcon 1500 cm$^2$ | $6.411\times10^5$ | 2.1 X |
| InVitro 1020 cm$^2$ | $7.182\times10^5$ | 2.4 X |
| InVitro 1700 cm$^2$ | $6.441\times10^5$ | 2.2 X |

The optimal parameters arrived at for growth of CH-SAH cells were to use Corning 850 cm$^2$ or Falcon 850 cm$^2$ roller with 350 ml media. Cells seeded at $3\times10^5$ per cm$^2$ would increase 4.6 and 4.0 times original density after 4 days propagation.

Example 2

The purpose of this experiment was to determine optimal parameters for infection of ILTV in CH-SAH cells. Parameters evaluated were multiplicity of infection (m.o.i.) and harvest time period.

ILT Challenge Virus as supplied by the USDA National Veterinary Services Laboratory and passaged 3 times in embryonated eggs has a titer of $1\times10^{6.5}$ $TCID_{50}$/ml. This material was composed of homogenized chorioallantoic membranes. It was frozen (−70° C.) and thawed (room temperature) twice. The inoculum was added at the same time as cells to 20 ml of media per flask. CH-SAH cells were seeded at $1\times10^5$ cells/cm$^2$ in 75 cm$^2$ Falcon filter vented flasks. The media used was described in Example 1 at 37° C., 2% $CO_2$ for the infection period. Harvest times used were 24, 48 and 72 hours. At the end of these time periods the flasks were placed at −30° C. until frozen. The flasks were then placed at room temperature until thawed. The virus homogenate was then titrated for activity at $TCID_{50}$/ml. M.O.I.'s used were 0.03, 0.006 and 0.0006.

| Har Time | MOI | Amt Inoc | Amt Har | Yield |
|---|---|---|---|---|
| 48 | 0.03 | $1\times10^{5.4}$ $TCID_{50}$ | $1\times10^{5.7}$ $TCID_{50}$ | 2.1 X |
| 72 | 0.03 | $1\times10^{5.4}$ $TCID_{50}$ | $1\times10^{6.1}$ $TCID_{50}$ | 5.3 X |
| 72 | 0.006 | $1\times10^{4.7}$ $TCID_{50}$ | $1\times10^{6.5}$ $TCID_{50}$ | 67.0 X |
| 72 | 0.0006 | $1\times10^{3.7}$ $TCID_{50}$ | ** | NA |

** = Virus level was below lower limit in titration assay
NA = Not Applicable

All the other harvest samples from time point 24 hours (all MOI's), and 48 hours (MOI 0.006 and 0.0006) were below the lower limit of the titration assay.

The optimal harvest parameters of infecting CAM ILTV unto CH-SAH cells were: seed cells at $1\times10^5$/cm$^2$, MOI of 0.006 and incubate for 72 hours before harvest.

Example 3

The purpose of this experiment was to determine the titer ($TCID_{50}$) of the virus harvested in Example 2.

Media used was previously described in Example 1. Plates used were Falcon Primeria 96-well MICROTEST III TM (flat-bottom) plates, catalog #3872. CH-SAH cells were split within a 24 hour period before the titration was performed (cells were still in lag phase, this was p.m. of Day −1). Seeding density was $1\times10^5$ cells/cm$^2$. Volume per well was 200 μl. Maintained at 37° C. and 5% $CO_2$.

Titration was started (Day 0) in the a.m. Virus samples were thawed and kept on ice until diluted. They were diluted in CH-SAH complete media. As each sample was diluted, b $1\times10^{-1}$ to $1\times10^{-8}$, it was placed at 4° C. until used After dilution of samples, 90 μl/well of media (10 μl remaining) was removed by use of a Costar multipipettor, same set of tips. This was done one sample at a time. 100 μl/well of virus dilution (4 replicates per dilution) was then added one sample at a time. Adsorption time of 1 hour (from last addition) was done at 37° C. and 2% $CO_2$. After the adsorption time, complete CH-SAH media was added, 100 μl/well, one sample at a time.

Plates and cells were observed for a 7-day period as follows:

Day 0: Pre-inoculation for % confluency (50%–70%).

Day 0: Post-inoculation for disturbance of monolayer (none).

Day 1: For pH and confluency (pH good, 80% confluency).

Day 3: As for Day 1.

Day 7: Briefly observed for % confluency (100%) and estimation of endpoint CPE (marked plate). Plate contents were then dumped and monolayer was fixed with 60% acetone/40% absolute ethanol.

Fluorescent antibody staining was done on these plates after washing with PBS. The chicken antisera was diluted 1:100 in PBS and incubated for 1 hour at 37° C. (SPAFAS antisera to ILTV). The plates were washed again with PBS and the conjugate was added for 1 hour at 37° C. (KPL FITC labeled affinity purified antibody to chicken IgG [H+L] produced in goats). The plates were washed again with PBS and then either read or stored at 4° C.

Any fluorescence was considered positive. Calculation of virus activity was done by the Reed Muench method (Reed, L. J., and H. Muench. "A simple method for estimating fifty percent endpoints" *Am. J. Hyg.* (1938) 27:493–497). The titer of this material in $TCID_{50}$/ml was listed in the table in Example 2.

Example 4

The purpose of the following experiments was to increase the titer ($TCID_{50}$/ml) of the virus harvested in Example 2. The method was to continually pass the virus in CH-SAH cells over a period of time (actual 32 passes).

CH-SAH cells were seeded in 75 cm$^2$ Corning flasks and were incubated at 37° C. with 5% $CO_2$ (pre infection). The media was the same as mentioned in Example 1. Seeding density varied from 30%–90% confluency of the monolayer at time of infection.

The inoculum was passed both cell-associated and cell-free. Cell-associated meaning that the cell monolayer was scraped in the presence of media and then a portion was inoculated directly into the next flask's media. Cell-free meaning that the cell monolayer was scraped in the presence of media and then freeze-thawed ($-70°$ C./RT) twice before inoculating into the next flask's media. The inoculum volume varied from entire contents (20 ml) to 1/30th of the harvest volume. Due to the frequent passing of virus and the fact that a titration takes 7 days, m.o.i. was not determined.

After inoculation the flasks were incubated at 37° C., 2% $CO_2$ until harvest. The incubation time varied from 1 day to 7 days, with daily observation. Harvest times were determined when maximal CPE was exhibited.

At the end of passaging this CH-SAH adapted virus material was titrated according to example 3. The titer of this material was $1 \times 10^{6.6}$ $TCID_{50}$/ml (geometric mean [GMT] of 8 samples).

Example 5

ILT Challenge Virus adapted to growth on CH-SAH as described in Example 4, was administered to a group of 7 week old specific pathogen free Leghorn chickens. A second group was given the parent (non-adapted) virus. Groups of 13 birds each were used. The parent virus and the CH-SAH adapted virus were given intratracheally at the same dose level each (target $=1\times 10^{4.3}$ $EID_{50}$). At the end of a 14 day observation period, the challenge virus group exhibited 100% morbidity (nasal discharge, moist rales, coughing, gasping, violent coughing and convulsive respiration including expulsion of blood clots) and 38% mortality. The CH-SAH adapted virus group exhibited 0% morbidity and 0% mortality. These results indicated that propagation in the CH-SAH cells attenuated the virus.

The attenuated virus was administered intraocularly ($1 \times 10^{3.9}$ $TCID_{50}$) to 4 week old specific pathogen free Leghorn chickens. On day 14 after vaccination the vaccinated group, along with an unvaccinated control group, was given ILT Challenge Virus intratracheally ($1 \times 10^{4.2}$ $TCID_{50}$). For 10 days after administration of the challenge virus the birds were observed. The control group exhibited 100% morbidity and 73% mortality while the attenuated virus group exhibited 0% morbidity and 0% mortality.

Comparative Example 1

Since both primary hepatocytes and macrophages have been shown to be infected by ILTV in vitro (Hughes and Jones (1988), Avian Pathology 17:295–303; Calnek et al. (1986), Avian Diseases 27:261–270), the retrovirus transformed cell lines of these cells were tested by Dr. Guo at Purdue University for propagation of ILTV.

Chicken cell line 249TK− was derived from an MC29 induced hepatoma and was obtained from Dr. R. F. Silva, Avian Diseases and Oncology Laboratory, United States Department of Agriculture, East Lansing, Mich. The 249TK− cells were grown in M199 medium (Gibco) supplemented with 10% FCS plus 2% chicken serum.

The macrophage cell line HD11 is a cell line transformed by the replication defective avian retrovirus reticuloendotheliosis virus (REV-T) and was obtained from Dr. V. Hinshaw, University of Wisconsin. HD11 cells were grown in RPMI 1640 (Gibco) supplemented with 5% FCS.

HD11, and 249TK− cells were infected with ILTV at an m.o.i. of 0.1. Primary embryonic liver cells served as control cells. Neither HD11 nor 249TK− cells showed any sign of infection within a week of incubation at 37° C. while the control cells showed complete CPE after only 2 days.

The lack of CPE or plaque formation does not exclude the possibility that ILTV DNA replicated in the cell but the viral assembly or egress step were blocked. To answer the question of whether ILTV DNA can replicate in the cell, ILTV-infected HD11 cells were tested for the presence of ILTV DNA. An ILTV DNA extraction from the cytoplasm of HD11 cells was performed 2 days post inoculation.

Extracted DNA was run on an agarose gel and blotted onto a nylon membrane. ILTV DNA derived from growth on primary embryonic hepatocytes served as a positive control. The DNAs were hybridized with a $^{32}$P-labeled ILTV EcoRI DNA fragment and exposed to a Kodak X-ray film. The positive control DNA gave a signal, but no positive hybridization signal could be found for DNA derived from either the cytoplasmic or the nuclear fraction of the infected macrophage cell line, though DNA has been present in all preparations as could be seen in the agarose gel prior to blotting. No ILTV DNA was synthesized in the macrophage cell line HD11. These findings lead to the conclusion that cells permissive for infection with ILTV, such as hepatocytes and macrophages, were rendered non-permissive for infection after transformation with avian retroviruses.

Comparative Example 2

QT35 is a chemically induced quail fibroblast cell line. The QT35 cells were obtained from Dr. R. Nodgreen, Solvay Animal Health, Inc., Mendota Heights, Minn.

QT35 was tested by Dr. Guo at Purdue University for its potential to propagate ILTV. QT35 cells were infected at an m.o.i, of 0.1 and incubated at 37° C. for 4 days. No signs of infection such as formation of syncytial cells or plaques were observed.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A continuous avian hepatocellular carcinoma cell line, wherein said cell line is CH-SAH, containing infectious laryngotracheitis virus.

2. Cells containing infectious laryngotracheitis virus prepared by culturing said virus in continuous avian hepatocellular carcinoma cell which is from the CH-SAH cell line.

3. A method for cultivating infectious laryngotracheitis virus comprising culturing said virus in a continuous avian hepatocellular carcinoma cell line, wherein said cell line is CH-SAH.

4. A method for obtaining infectious laryngotracheitis virus comprising (i) infecting a continuous avian hepatocellular cell line, wherein said cell line is CH-SAH, with infectious laryngotracheitis virus, (ii) culturing said virus, and (iii) recovering virus produced thereby.

5. The method according to claim 4, wherein said recovery step is performed after said infected cells exhibit a maximal cytopathic effect.

* * * * *